(12) United States Patent
Satchivi et al.

(10) Patent No.: US 8,673,817 B2
(45) Date of Patent: Mar. 18, 2014

(54) CONTROL OF PHENOXYALKANOIC ACID HERBICIDE-RESISTANT WEEDS WITH 4-AMINO-3-CHLORO-6-(4-CHLORO-2-FLUORO-3-METHOXYPHENYL) PYRIDINE-2-CARBOXYLIC ACID AND ITS SALTS OR ESTERS

(75) Inventors: Norbert M. Satchivi, Westfield, IN (US); Paul R. Schmitzer, Indianapolis, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/289,008

(22) Filed: Nov. 4, 2011

(65) Prior Publication Data

US 2012/0115727 A1    May 10, 2012

Related U.S. Application Data

(60) Provisional application No. 61/410,450, filed on Nov. 5, 2010.

(51) Int. Cl.
*A01P 13/00* (2006.01)
*A01N 43/40* (2006.01)

(52) U.S. Cl.
USPC ........................................................ 504/260

(58) Field of Classification Search
USPC ............................................................ 504/260
See application file for complete search history.

(56) References Cited

U.S. PATENT DOCUMENTS

| 7,314,849 | B2 | 1/2008 | Balko et al. | |
|---|---|---|---|---|
| 7,838,733 | B2 | 11/2010 | Wright et al. | |
| 2007/0179060 | A1* | 8/2007 | Balko et al. | 504/193 |
| 2010/0137137 | A1* | 6/2010 | Rosinger et al. | 504/105 |
| 2011/0203017 | A1 | 8/2011 | Wright et al. | |

FOREIGN PATENT DOCUMENTS

WO    WO2009/029518 A2 *  3/2009 ............. 504/260
WO    PCT/US2011/059252    11/2011

OTHER PUBLICATIONS

Jordan et al. Influence of Application Variables on Efficacy of Glyphosate. Weed Technology. 1997 vol. 11:354-365.
Hager et al. Herbicide Formulations and Calculations: Active Ingredient or Acid Equivalent? (2000) http://bulletin.ipm.illinois.edu/pastpest/articles/200002j.html.
Duran-Prado et al. Molecular basis of resistance to sulfonylureas in *Papaver rhoeas*. Pesticide Biochemistry and Physiology 79 (2004) 10-17.

* cited by examiner

*Primary Examiner* — Janet Epps-Smith
*Assistant Examiner* — Audrea Buckley
(74) *Attorney, Agent, or Firm* — Robert Chang

(57) ABSTRACT

4-Amino-3-chloro-6-(4-chloro-2-fluoro-3-methoxyphenyl) pyridine-2-carboxylic acid and its salts or esters effectively controls phenoxyalkanoic acid herbicide-resistant weeds despite having the same mode of action as phenoxyalkanoic acid herbicides.

2 Claims, No Drawings

CONTROL OF PHENOXYALKANOIC ACID HERBICIDE-RESISTANT WEEDS WITH 4-AMINO-3-CHLORO-6-(4-CHLORO-2-FLUORO-3-METHOXYPHENYL) PYRIDINE-2-CARBOXYLIC ACID AND ITS SALTS OR ESTERS

CROSS REFERENCE TO RELATED APPLICATIONS

This application claims the benefit of U.S. Provisional Patent Application Ser. No. 61/410,440 filed Nov. 5, 2010.

FIELD OF THE INVENTION

This invention concerns the use of 4-amino-3-chloro-6-(4-chloro-2-fluoro-3-methoxyphenyl)pyridine-2-carboxylic acid and its salts or esters to selectively control phenoxyalkanoic acid herbicide-resistant weeds.

BACKGROUND OF THE INVENTION 2,4-D, (2,4-dichlorophenoxy)acetic acid, is a phenoxyacetic acid herbicide, and its herbicidal activity is described in *The Pesticide Manual*, Fifteenth Edition, 2009. 2,4-D, which acts as a growth inhibitor, provides post-emergent control of many annual and perennial broadleaf weeds particularly in cereals and turf. 2,4-D has been in wide use since its introduction in the 1940s and certain weeds have developed a tolerance to both it and to other herbicides whose mode of action is that of acting as an auxinic growth inhibitor. Resistance of corn poppy (*Papaver rhoeas*) to 2,4-D is well documented (Torra et al., 2010. *Evaluation of herbicides to manage herbicide-resistant corn poppy (Papaver rhoeas) in winter cereals. Crop Protection.* 29, 731-736). It would be desirable to find an effective replacement for 2,4-D for the post-emergent control of phenoxyalkanoic acid herbicide-resistant weeds.

SUMMARY OF THE INVENTION

It has now been surprisingly found that 4-amino-3-chloro-6-(4-chloro-2-fluoro-3-methoxyphenyl)pyridine-2-carboxylic acid (Compound I), a pyridine carboxylic acid herbicide which is also an auxinic growth inhibitor, and its salts or esters can effectively control weeds that are resistant to phenoxyalkanoic acid herbicides. The present invention concerns a method of controlling the growth of weeds that are resistant to phenoxyalkanoic acid herbicides which comprises contacting the phenoxyalkanoic acid herbicide-resistant weeds or the locus thereof with an herbicidally effective amount of 4-amino-3-chloro-6-(4-chloro-2-fluoro-3-methoxyphenyl)pyridine-2-carboxylic acid or its salts or esters.

DETAILED DESCRIPTION OF THE INVENTION

4-Amino-3-chloro-6-(4-chloro-2-fluoro-3-methoxyphenyl)pyridine-2-carboxylic acid (Compound I) is a pyridine carboxylic acid herbicide, and its herbicidal activity is described in U.S. Pat. No. 7,314,849 (B2). 4-Amino-3-chloro-6-(4-chloro-2-fluoro-3-methoxyphenyl)pyridine-2-carboxylic acid is primarily used as a post-emergent herbicide for the control of broadleaf weeds in cereals by acting as an auxinic growth inhibitor. Suitable salts include those derived from alkali or alkaline earth metals and those derived from ammonia and amines. Preferred cations include sodium, potassium, magnesium, and ammonium cations of the formula:

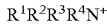

wherein $R^1$, $R^2$, $R^3$ and $R^4$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R^1$, $R^2$, $R^3$ and $R^4$ are sterically compatible. Additionally, any two of $R^1$, $R^2$, $R^3$ and $R^4$ together may represent an aliphatic difunctional moiety containing one to twelve carbon atoms and up to two oxygen or sulfur atoms. Salts of Compound I can be prepared by treatment of the carboxylic acid with a metal hydroxide, such as sodium hydroxide, with an amine, such as ammonia, trimethylamine, diethanolamine, 2-methylthiopropylamine, bisallylamine, 2-butoxyethylamine, morpholine, cyclododecylamine, or benzylamine or with a tetraalkylammonium hydroxide, such as tetramethylammonium hydroxide or choline hydroxide Amine salts are often preferred forms of Compound I because they are water-soluble and lend themselves to the preparation of desirable aqueous based herbicidal compositions.

Suitable esters include those derived from $C_1$-$C_{12}$ alkyl, $C_3$-$C_{12}$ cycloalkyl, $C_3$-$C_{12}$ alkenyl, $C_3$-$C_{12}$ alkynyl alcohols or $C_7$-$C_{10}$ aryl-substituted alkyl alcohols, such as methyl alcohol, isopropyl alcohol, 1-butanol, 2-ethylhexanol, butoxyethanol, methoxypropanol, allyl alcohol, propargyl alcohol, cyclohexanol or unsubstituted or substituted benzyl alcohols. Benzyl alcohols may be substituted with from 1-3 substituents independently selected from halogen, $C_1$-$C_4$ alkyl or $C_1$-$C_4$ alkoxy. Esters can be prepared by coupling of the carboxylic acid of Compound I with the alcohol using any number of suitable activating agents such as those used for peptide couplings such as dicyclohexylcarbodiimide (DCC) or carbonyl diimidazole (CDI), by reacting the corresponding acid chloride of Compound I with an appropriate alcohol or by reacting Compound I with an appropriate alcohol in the presence of an acid catalyst.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include non-germinated seeds, emerging seedlings, above and below ground plant parts such as shoots, roots, tubers, rhizomes and the like, and established vegetation.

Herbicidal activity is exhibited by 4-amino-3-chloro-6-(4-chloro-2-fluoro-3-methoxy-phenyl)pyridine-2-carboxylic acid or its esters when it is applied directly to the locus of the plant before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, 4-amino-3-chloro-6-(4-chloro-2-fluoro-3-methoxyphenyl)pyridine-2-carboxylic acid or its esters is applied post-emergence to control weeds that are resistant to phenoxyalkanoic acid herbicides at a rate from about 4 grams acid equivalent per hectare (gae/ha) to about 70 gae/ha.

4-Amino-3-chloro-6-(4-chloro-2-fluoro-3-methoxyphenyl)pyridine-2-carboxylic acid and its esters are generally employed in combination with known herbicide safeners such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenylsulfonylbenzoic acid amides, to enhance selectivity. Cloquintocet (mexyl) is especially preferred.

While it is possible to utilize 4-amino-3-chloro-6-(4-chloro-2-fluoro-3-methoxyphenyl)pyridine-2-carboxylic acid or its esters directly as a herbicide, it is preferable to use it in mixtures containing an herbicidally effective amount of the compound along with at least one agriculturally acceptable adjuvant or carrier. Suitable adjuvants or carriers should not be phytotoxic to the perennial grasses, particularly at the concentrations employed in applying the compositions for grass growth regulation, and should not react chemically with the compounds or other composition ingredients. Such mixtures can be designed for application directly to grasses or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsifiable concentrates or suspensions. They can also be provided as a pre-mix or tank mixed. They can also be provided as a pre-mix or tank mixed.

Suitable agricultural adjuvants and carriers that are useful in preparing the herbicidal mixture are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG (400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, dibutyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the herbicidal mixtures. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., N.Y., 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of 4-amino-3-chloro-6-(4-chloro-2-fluoro-3-methoxyphenyl)-pyridine-2-carboxylic acid or its esters in the herbicidal mixture is generally from 0.001 to 98 percent by weight. Concentrations from 5 to 90 percent by weight are often employed. In compositions designed to be employed as concentrates, the active ingredients are generally present in a concentration from 5 to 98 weight percent, preferably 5 to 90 weight percent. Such compositions are typically diluted with an inert carrier, such as water, before application. The diluted compositions usually applied to grasses or the locus of grasses generally contain 0.0001 to 1 weight percent active ingredient and preferably contain 0.001 to 0.1 weight percent.

The present compositions can be applied to weeds or their locus by the use of conventional ground or aerial dusters, sprayers, and granule applicators, by addition to irrigation water, and by other conventional means known to those skilled in the art.

The following examples illustrate the present invention. Evaluation of Postemergence Herbicidal Activity on Susceptible and Phenoxyalkanoic Acid Herbicide-Resistant Weeds Seeds of the phenoxyalkanoic acid herbicide-resistant and susceptible plant species were planted in Sun Gro Metro-Mix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days (d) in a greenhouse with an approximate 14-hour (h) photo-period which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of the acid or esters of 4-amino-3-chloro-6-(4-chloro-2-fluoro-3-methoxyphenyl)pyridine-2-carboxylic acid (Compound I) and 2,4-D, mecoprop and 2-(4-chloro-2-methyl-phenoxy)acetic acid (MCPA) alone. Weighed amounts of the herbicides were dissolved in a volume of 97:3 volume-per-volume (v/v) acetone/dimethylsulfoxide (DMSO) to obtain concentrated solutions. If the test compound did not dissolve readily, the mixture was warmed and/or sonicated. The concentrated solutions of the test compound were diluted with the addition of an aqueous mixture containing acetone, water, isopropyl alcohol, DMSO, Agri-Dex crop oil concentrate, and Triton® X-77 surfactant in a 64.7:26.0:6.7:2.0:0.7:0.01 v/v ratio. Test compounds were diluted to the appropriate application rate with a dilution solution which was prepared by mixing the appropriate volume of 97:3 v/v acetone/DMSO and the appropriate volume of an aqueous mixture containing acetone, water, isopropyl alcohol, DMSO, Agri-Dex crop oil concentrate, and Triton® X-77 surfactant in a 64.7:26.0:6.7:2.0:0.7:0.01 v/v ratio. Compound requirements are based upon a 12 mL application volume at a rate of 187 liters per hectare (L/ha). Spray solutions of 2,4-D, mecoprop and MCPA were prepared by diluting an aliquot of the concentrated herbicide with an aqueous mixture containing 1.25% v/v Agri-Dex. 2,4-D, mecoprop and MCPA were applied at 1×, 2× and 4× of the recommended application rate.

Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 centimeters (cm)) above average plant canopy. Control plants were sprayed in the same manner with the solvent blank.

The treated plants and control plants were placed in a greenhouse as described above and watered by sub-irrigation to prevent wash-off of the test compounds. After 20-22 d, the condition of the test plants as compared with that of the control plants was determined visually and scored on a scale of 0 to 100 percent where 0 corresponds to no injury and 100 corresponds to complete kill.

Some of the compounds tested, application rates employed, plant species tested, and results are given in Table 1 through Table 4.

TABLE 1

Activity of Compound I on susceptible and phenoxyalkanoic acid herbicide-resistant corn poppy

| Application Rate (g ae/ha) Compound I | PAPRH-S1F00101 | PAPRH-S4F00101 | PAPRH-S4F00103 | PAPRH-S2F01502 | PAPRH-Susceptible |
|---|---|---|---|---|---|
| 7.5 | 90 | 88 | 78 | 93 | 95 |
| 10 | 90 | 94 | 95 | 94 | 97 |

TABLE 2

Activity of 2,4-D on susceptible and phenoxyalkanoic acid herbicide-resistant corn poppy

| Application Rate (g ae/ha) 2,4-D | PAPRH-S1F00101 | PAPRH-S4F00101 | PAPRH-S4F00103 | PAPRH-S2F01502 | PAPRH-Susceptible |
|---|---|---|---|---|---|
| 800 | 21 | 22 | 21 | 15 | 85 |
| 1600 | 16 | 42 | 19 | 53 | 94 |
| 3200 | 50 | 33 | 59 | 51 | 99 |

TABLE 3

Activity of MCPA on susceptible and phenoxyalkanoic acid herbicide-resistant corn poppy

| Application Rate (g ae/ha) MCPA | PAPRH-S1F00101 | PAPRH-S4F00101 | PAPRH-S4F00103 | PAPRH-S2F01502 | PAPRH-Susceptible |
|---|---|---|---|---|---|
| 800 | 14 | 28 | 23 | 28 | 70 |
| 1600 | 23 | 37 | 40 | 14 | 89 |
| 3200 | 57 | 60 | 57 | 58 | 100 |

TABLE 4

Activity of mecoprop on susceptible and phenoxyalkanoic acid herbicide-resistant corn poppy

| Application Rate (g ae/ha) Mecoprop-P | PAPRH-S1F00101 | PAPRH-S4F00101 | PAPRH-S4F00103 | PAPRH-S2F01502 | PAPRH-Susceptible |
|---|---|---|---|---|---|
| 800 | 27 | 27 | 21 | 23 | 56 |
| 1600 | 54 | 53 | 65 | 66 | 79 |
| 3200 | 78 | 80 | 94 | 93 | 98 |

PAPRH = *Papaver rhoeas* (corn poppy)
g ae/ha = grams acid equivalent per hectare

What is claimed is:

1. A method of controlling the growth of weeds that are resistant to phenoxyalkanoic acid herbicides, wherein the weeds are corn poppies, comprising contacting the weeds or a locus of the weeds with an herbicidally effective amount of 4-amino-3-chloro-6-(4-chloro-2-fluoro-3-methoxyphenyl) pyridine-2-carboxylic acid or a salt or ester thereof.

2. The method of claim 1 in which the 4-amino-3-chloro-6-(4-chloro-2-fluoro-3-methoxyphenyl)pyridine-2-carboxylic acid or the salt or ester thereof is applied at a rate from about 4 gae/ha to about 70 gae/ha.

* * * * *